(12) United States Patent
Smith et al.

(10) Patent No.: US 6,275,566 B1
(45) Date of Patent: Aug. 14, 2001

(54) MINIATURE X-RAY TUBE WITH VOLTAGE SELECTIVE ELECTRODES

(75) Inventors: Leif Smith; Lars Tenerz; Jonas Tiren, all of Uppsala; Pelle Rangsten, Storvreta, all of (SE)

(73) Assignee: Radi Medical Technologies AB, Uppsala (SE)

( * ) Notice: Subject to any disclaimer, the term of this patent is extended or adjusted under 35 U.S.C. 154(b) by 0 days.

(21) Appl. No.: 09/557,402

(22) Filed: Apr. 24, 2000

(30) Foreign Application Priority Data

Mar. 31, 2000 (EP) .................................................. 00850058

(51) Int. Cl.[7] .................................................. H01J 35/00
(52) U.S. Cl. .............................. 378/122; 378/65; 378/124
(58) Field of Search .................................... 378/122, 124, 378/65

(56) References Cited

U.S. PATENT DOCUMENTS 5,854,822  12/1998  Chornenky et al. .................. 378/122

FOREIGN PATENT DOCUMENTS

WO 98/48899  11/1998  (WO) .
WO 99/45563  9/1999  (WO) .

*Primary Examiner*—Craig E. Church
(74) *Attorney, Agent, or Firm*—Foley & Lardner

(57) ABSTRACT

A method and a system for x-ray treatment of, for example, cancer or restenosis prevention inside a living body is disclosed. A miniature x-ray tube (1) is provided with at least one pair of electrodes (6, 8), the electrodes alternatingly serving as anode and cathode, respectively. A power supply (13) is connected to the electrodes, and a switching unit of the power supply alternates the electrical potential across the electrodes. With the x-ray tube according to the invention the temperature increase at the site of treatment is limited, thereby providing an effective treatment without unduly prolonged treatment duration.

15 Claims, 6 Drawing Sheets

MINIATURE X-RAY TUBE WITH VOLTAGE SELECTIVE ELECTRODES

The applicants hereby claim the benefit of prior European Application No. 00850058.9, filed Mar. 31, 2000. The entire contents of this European application are incorporated by reference.

FIELD OF THE INVENTION

The present invention relates to a miniature x-ray tube. In particular, the miniature x-ray tube according to the invention is useful for prevention of restenosis and for treating diseases, such as cancer, in a living body.

BACKGROUND OF THE INVENTION

In treating stenosis in coronary arteries, a restenosis occurs in 30–60% of the cases. It is known that a treatment with beta- or gamma- (x-ray) radiation will decrease the occurrence of restenosis substantially. Methods to apply this radiation to the treated stenosis are presently subject to intensive research.

Another example of an application of the present invention is treatment of cancer tumours where it is desired to deliver radiation locally.

The use of radioactive pellets or balloons etc. to introduce radioactive isotopes is known. The radioactive isotopes are introduced via a catheter, a needle or similar to the treated area. Such methods have some drawbacks, such as limited half-life of the isotope as well as the fact that the devices used emit radiation continuously. Such devices sometimes require substantial efforts to control radiation in the environment outside the patient and also exhibit problems with dose control.

The importance of controlling the radiation distribution along the vessel and of ensuring that only tissue that has been treated by coronary angioplasty will receive radiation while as little as possible radiation is applied to healthy tissue has been recognised. Thus, Novoste Corp. has introduced an array of isotope elements, enabling the radiated length of the vessel to be predetermined stepwise.

One known way to overcome some of the above drawbacks is the use of a miniature electrical x-ray tube including a cold cathode. Such a tube may be switched on and off due to its electrical activation. An example of such an x-ray tube is described in the U.S. Pat. No. 5,854,822.

However, the conventional miniature electrical x-ray tubes exhibit a problem in that the delivery of radiation has a very limited spatial extension. These radiation sources can in essence be regarded as approximately "point like" radiation sources.

Another problem present with a conventional miniature electrical x-ray tube is the dissipated heat. The temperature increase with respect to the body temperature should not be high enough to produce a local temperature exceeding approximately 41° C.

One way to handle the dissipated heat is to provide cooling by flushing a saline solution onto the tube. Cooling by flushing exhibits the problem of enlarging the geometry since the saline must be delivered to the source of heat and therefore must be directed by some means that inevitably will occupy space. Also, a flow through a catheter has to be established and maintained to cool the x-ray tube which is generally awkward.

Another way to reduce the dissipated heat is the use of a pulsed source wherein the electrically activated tube is turned on intermittently. However, a pulsed source exhibits the drawback that the treatment time will be prolonged correspondingly, since the received dose must be held constant. This is costly and increases the discomfort for the patient.

Yet another way to reduce the dissipated heat is to apply a sufficiently low current to the conventional x-ray tube. In consequence, the treatment time has to be correspondingly increased in order to apply the appropriate dose of x-ray radiation. This, of course, is disadvantageous in that the longer treatment time is inconvenient to the patient and calls for raised costs in the hospital.

Yet another problem experienced with the conventional techniques including miniature electrical x-ray tubes is the erosion of the electrode material. As the target is bombarded by high-energy particles, the impacts will tear away atoms from the surface. If these atoms are ionized they may be transported away from the target to be deposited on the cathode or on other parts of the interior of the x-ray tube.

Therefore, there is a need for an improved miniature electrical x-ray tube.

SUMMARY OF THE INVENTION

It is an object of the present invention to provide an improved miniature electrical x-ray tube.

This object is obtained with an x-ray tube according to claim 1.

With the x-ray tube of the invention, the emitted x-ray dose is alternatingly emitted from more than one cathode. Thus, for each point in time there is always a cathode that is not active, thereby allowing its temperature to be cooled. At the same time, there is another cathode emitting radiation, thereby providing a substantially continuous radiation. Therefore, the maximum working temperature of each cathode will be lower than the temperature of a conventional cathode for the same radiated x-ray dose and, consequently, the problem of dissipated heat is significantly reduced.

At the same time, the x-ray tube of the present invention provides considerably reduced treatment time as compared to a conventional pulsed x-ray tube for the same radiation dose.

In addition to these advantages, the x-ray tube of the invention provides a tube with at least two sources of radiation, making it possible to cover a larger area with radiation during the treatment. This feature is enhanced in multi-cell embodiments of the invention, as will be described further below.

DETAILED DESCRIPTION OF EMBODIMENTS

Figure 10:
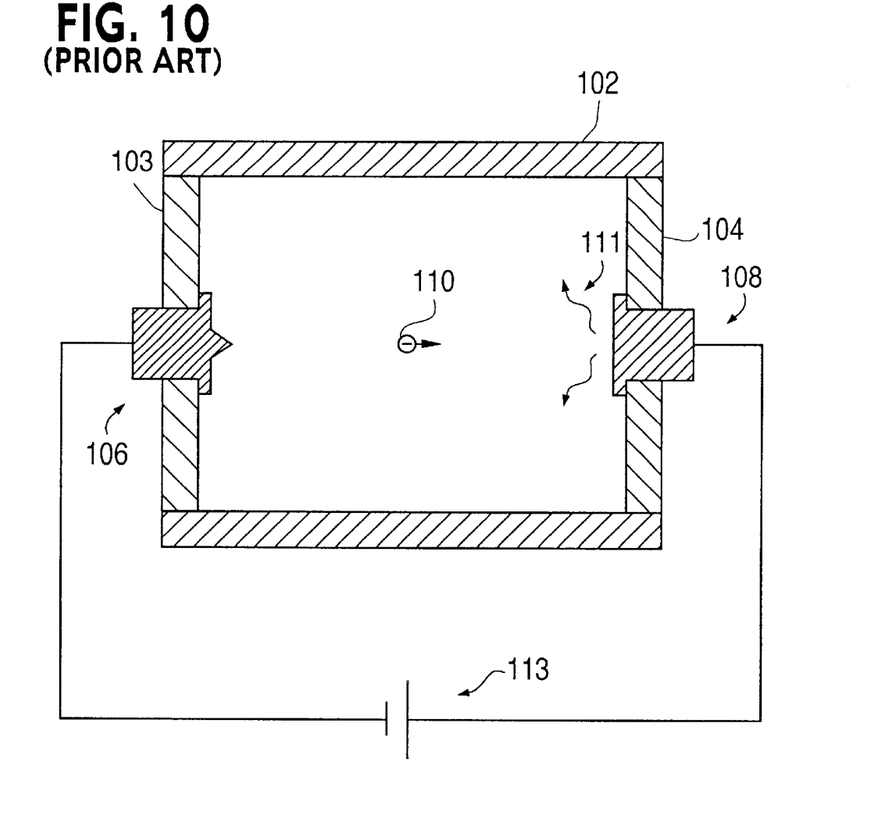
FIG. 10 is a schematic cross-sectional view of a prior art x-ray tube.

An example of a conventional, prior art miniature x-ray tube is illustrated in the schematic cross-sectional view of FIG. 10. The tube has an enclosure consisting of a hollow cylindrical tube 102 of an x-ray transparent material, and end walls 103, 104 (although other arrangements, such as end walls integrated with the tubular enclosure are also known). The enclosure is hermetically sealed, and a vacuum is provided inside the tube. A cathode 106, adapted to emit electrons, and an anode 108, the latter adapted to emit x-ray radiation, penetrates through respectively opposite ends of the tube. When the cathode is connected to the negative potential of a high voltage source 113 and the anode is connected to the corresponding positive potential of the voltage source, electrons 110 will be emitted from the cathode to impact into the anode. As the electrons hit the anode, x-ray radiation 111 is emitted from the anode. The x-ray transparent enclosure allows the x-ray radiation to be delivered to a patient.

According to the present invention, instead of having a dedicated cathode and a dedicated anode, the miniature X-ray tube is provided with at least one pair of electrodes wherein each electrode is adapted to alternately serve as cathode and anode, respectively. More specifically, at a first point in time one of the electrodes of the pair acts as the cathode while the other electrode acts as the anode. Then, at a second point in time, the electrode that previously acted as the cathode will now become the anode, and vice versa. Since the heat is essentially dissipated at the anode, and the position of the anode in this way is altering between two physical positions during treatment, the heat dissipation is reduced at each anode position and, in consequence, the temperature at each anode is reduced due to the repeated cooling intervals provided between the active intervals.

The invention shall now be described in detail by way of embodiments. Of course, the described embodiment should not be viewed as limiting for the scope of the invention.

A first and basic embodiment of the present invention is schematically illustrated with reference to FIG. 1 and 2, wherein is shown a single cell x-ray tube 1. The single cell x-ray tube is defined by an enclosure 2 of a material that is penetrable by x-rays, such as glass, silicon carbide, $Al_2O_3$, quartz, diamond, boron nitride, pyrolytic boron nitride etc., a first insulating end wall 3 at one end side of the tube, and a second insulating end wall 4 at the other end side. Although any suitable shape of the enclosure could be used, such as bulb like, spherical or hollow with quadrangular cross section, it is preferred to form the enclosure as a tube, i.e. as a hollow cylinder with a circular cross section or with a similar cross sectional shape, such as hexagonal.

The parts are joined by vacuum tight sealing. This may be achieved by using vacuum grade epoxies, using vacuum brazing with appropriate alloys (typically a Ag/Cu alloy) or by using glass frit. The final assembly must obviously be carried out in vacuum.

Figure 11:
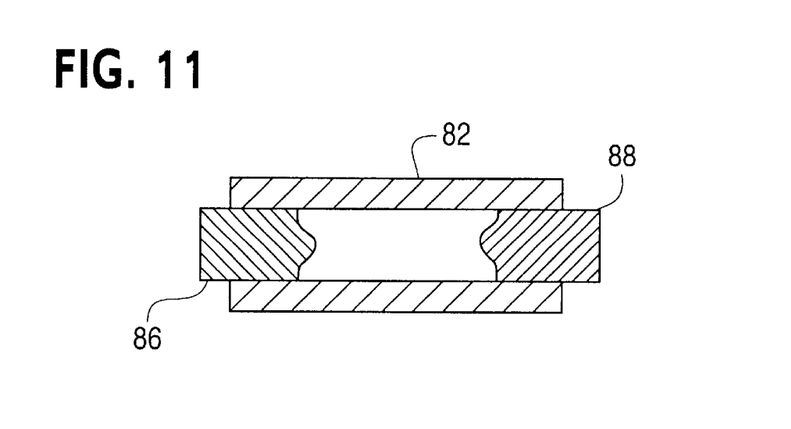
FIG. 11 is a schematic cross-sectional view of an x-ray tube according to the invention having no end walls.

The end walls, which typically are made of a similar material as the enclosure, could in fact be integrated with the tubular enclosure, or even omitted in a case of a tube having an inner diameter of the same order as the diameter of the electrodes. An example of a miniature x-ray tube according to the invention having no dedicated end walls is shown in FIG. 11, wherein a tubular enclosure 82 holds two electrodes 86, 88.

Again referring to FIG. 1, a vacuum 5 is established in the tube.

A first electrode 6 penetrates through the first end wall 3. In the embodiment shown, the electrode 6 consists of a conductor section 6A for attachment to an external power source 13 via a conductor 14, and an internal section 6B inside the x-ray tube. The conductor section 6A is made from a suitable conducting material, such as copper. The internal section 6B is made from a material suitable for emitting x-ray energy when hit with electrons, such as tungsten, iridium or gold.

As shown, the internal section 6B could be formed with a tip 7. The tip-formed shape provides a useful emitting area when the electrode acts as an emitter, as will be described below, although other shapes are useful as well, such as planar or hemispherical with a smooth or roughened surface.

The power source 13 is a switching power supply, i.e. a power source provided with a switching unit for providing an alternating voltage potential.

A second electrode 8, generally similar or identical in shape to the first electrode 6, penetrates through the second side end wall 4. Thus, in the embodiment shown the electrode 8 has two sections corresponding to the sections 6A, 6B of the other electrode 6. The second electrode 8 is connected to the switching power supply 13 via a conductor 12.

Of course, it is not necessary that each electrode consists of two sections. It could be made in one piece, or several sections as well, In use, the switching power supply 13 applies an alternating voltage across the electrodes.

More specifically, during a first interval the first electrode 6 is provided with a negative electrical potential with respect to the other electrode 8, thereby making the first electrode 6 a cathode, and consequently the second electrode 8 is provided with a positive electrical potential with respect to the first electrode 6, thereby making the second electrode 8 an anode.

Figure 1:
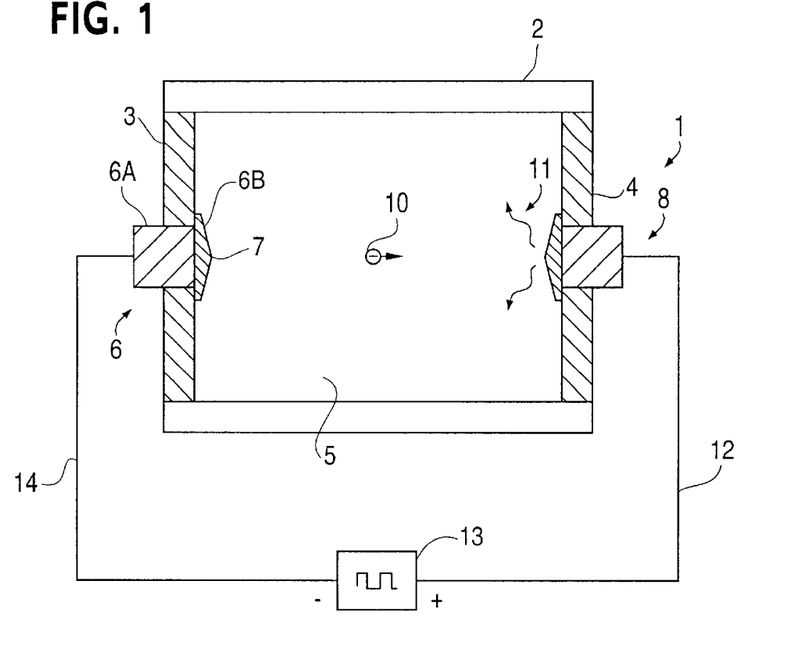
FIG. 1 is a schematic cross-sectional view of a first embodiment of an x-ray tube according to the present invention in a first state of operation.
Figure 2:
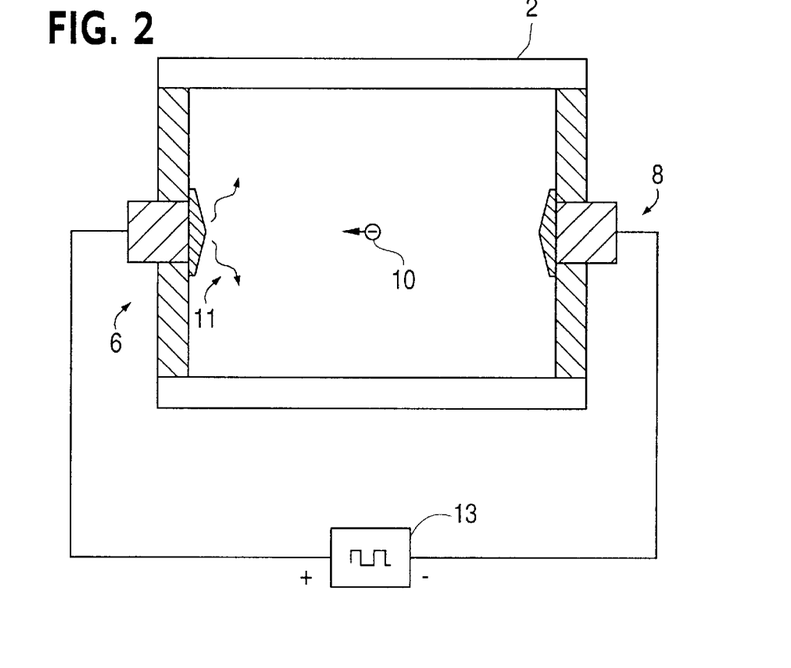
FIG. 2 is a schematic cross-sectional view of a first embodiment of an x-ray tube according to the present invention in a second state of operation.

During a second interval following the first, as illustrated in FIG. 2 showing the x-ray tube of FIG. 1 in a state of reversed electrical potential, the potentials are switched by the switching power supply 13. Thus, the first electrode 6 is provided with a positive electrical potential, thereby making it an anode, while the second electrode 8 is provided with a negative electrical potential, thereby making it a cathode.

This switching of the electrical potentials continues as long as the x-ray tube is activated. The voltage levels and switching frequency are selected to suit the application at hand.

During each interval, the electrical potential difference applied between the cathode and the anode creates a flow of electrons 10 from the electrode presently being the cathode to the electrode presently being the anode. When the electrons hit the electrode presently being the anode, energy is released in the form of heat and x-ray radiation 11.

The outer diameter of the x-ray tube according to the present invention should generally be within a range of about 0.5 to 3 mm, in order to fit into the vessels for treatment which typically have inner diameters within a range of about 1 to 5 mm. The longitudinal length of a stenosis is typically in the range of 1 to 100 mm.

The treatment duration is selected to provide an adequate radiation dose. For example, a radiation dose suitable for treatment of coronary stenosis typically is in the range of 10–40 Gy, while a radiation dose suitable for treatment of cancer typically is in the range of 1–100 Gy.

With the x-ray tube and the switching power supply of the present invention, essentially the same energy output per unit of time is obtained as with a corresponding conventional continuously radiating x-ray tube. However, due to the switching scheme the heat developed during operation is divided between two anode areas, thereby reducing the temperature increase. In consequence, also the material erosion of the electrodes is correspondingly reduced.

On the other hand, compared to a corresponding conventional pulsed x-ray tube, the treatment time will be significantly reduced, as long as heat dissipation is limiting the dose rate.

Furthermore, due to the axial distance between the switching target areas, i.e. the sources of x-ray radiation, an axial extension corresponding to the distance between the electrode targets areas will be obtained. Therefore, a x-ray tube according to the present invention distributes the x-ray radiation over a larger target area than does a conventional tube having a point-like x-ray source.

Figure 13:
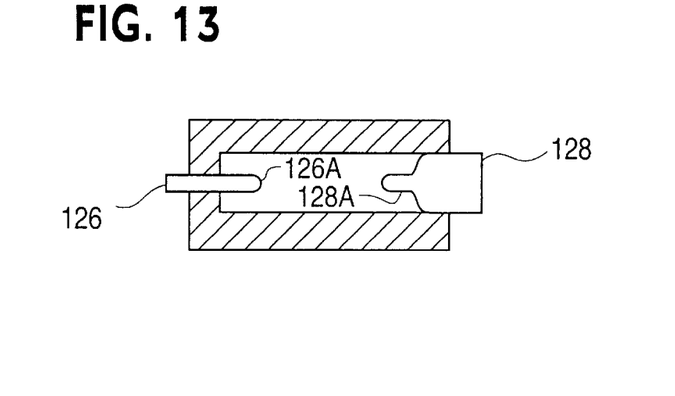
FIG. 13 is another embodiment of an x-ray tube according to the present invention.

The electrodes at each end should be designed to have generally the same mutual electrical properties when they act as anodes as well as cathodes, respectively. Although preferred for manufacturing reasons, this does not require the electrodes to be identical. An example of this is shown in FIG. 13, wherein a first electrode 126 differs from a second electrode 128, except for a distal operative section 126A which is similar to a distal operative section 128A of the second electrode. The operative sections 126A, 128A act alternatively as anodes and cathodes. In fact, also the operative sections could be of different design, as long as their anode and cathode properties are mutually similar.

In a very basic embodiment, as illustrated in FIGS. 1 and 2, the single cell x-ray tube of the present invention will be emitting radiation from two locations (as opposed to one in the conventional x-ray tubes) and the heat will be generated at the same two locations (as opposed to one).

Figure 3:
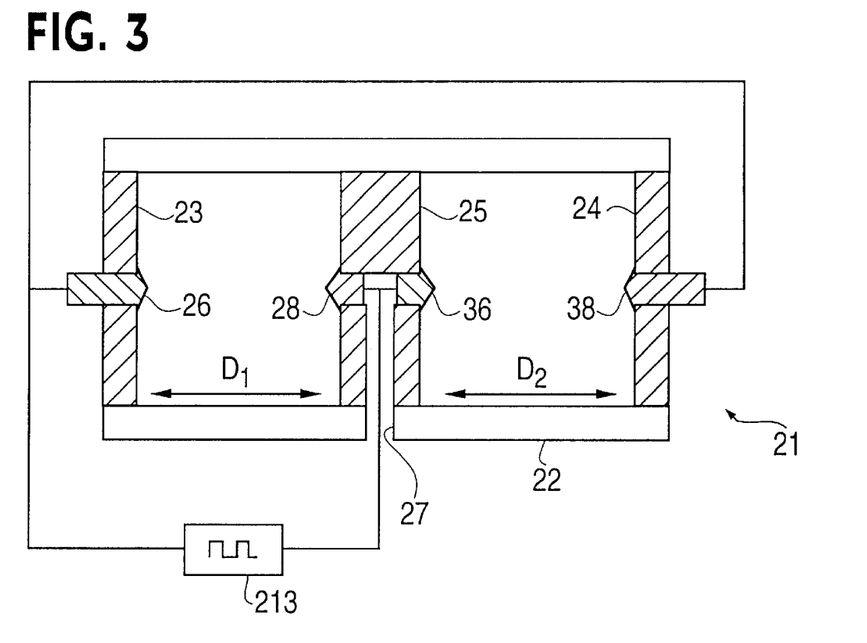
FIG. 3 is a schematic cross-sectional view of a second embodiment of an x-ray tube according to the present invention.

In a second embodiment of the present invention, as is illustrated in FIG. 3, two x-ray cells according to the invention are arranged to form one x-ray radiating device. The x-ray tube 21 according to the second embodiment includes a tube enclosure 22 permeable for x-ray radiation, a first end wall 23, a second end wall 24, an intermediate wall 25, a first pair of electrodes 26, 28 one of which 26 is mounted in the first end wall 23 and the other 28 is mounted in the intermediate wall 25, a second pair of electrodes 36, 38 one of which 36 is mounted in the intermediate wall 25 and the other 38 is mounted in the second end wall 24, and an electronic unit 213.

The electronic unit 213 is a switching power supply, similar to what has been described for the first embodiment, for providing a voltage of switching polarities. One output from the electronic unit 213 is connected to the one electrode of each pair of electrodes, respectively, while the other output is connected to the other electrode of each pair of electrodes, respectively.

Thus, in the embodiment shown in FIG. 3, one electrode 28 of the first pair and one electrode 36 of the second pair are commonly connected to one terminal of the electronic unit 213, which is schematically shown in FIG. 3 with a wire running through a channel 27 extending through the tube enclosure 22 and the intermediate wall 25.

As is easily understood, by switching the polarity of the voltage applied by the electronic unit 213 in a manner corresponding to what has been described above, x-ray radiation will be emitted from the electrodes 28, 36 during a first interval of each switching cycle, and from the electrodes 26, 38 during a second interval of the switching cycle.

This will enable the heat to be further distributed, as compared to the first embodiment therefore enabling a larger dose rate and a shorter treatment time if the generation of radiation otherwise is limited by heat dissipation.

It should be understood that a further integration of an arbitrary number of x-ray cells is possible according to this principle, as long as it is practical to do so. Thus, any suitable number of x-ray cells, could be arranged in a row, in parallel or in any other pattern similar to the second embodiment.

Also, with the second embodiment an even larger area could be covered with x-ray radiation as compared to the first embodiment due to the four emitting surfaces.

This embodiment of the x-ray tube may also be used in such a way that only one of the integrated tubes is selected to radiate. This could, for example, be achieved by introducing a switch (not shown) to connect or disconnect the electrode 38 of FIG. 3, or alternately the electrode 26. If a larger number of such x-ray cells are integrated into one x-ray tube it is understood that an arbitrary number of these may be selected. This will further enhance the degree of freedom when using the device.

Thus, according to the embodiment of FIG. 3, radiation is emitted at four locations while needing only three electrical points, thereby providing for a simple electric connection.

It should also be noticed that it is possible to use different electrode distances D1, D2 for each individual x-ray cell. This makes it possible to use either of these chambers to achieve different radiation energies from the different parts of the tube while still keeping the current to a desired low level, thus limiting the heat dissipation.

According to a third embodiment of the present invention, electrodes being specifically designed to serve as cathodes and anodes, alternatively, are provided in the x-ray tube. More specifically, according to the third embodiment electrode materials are selected and disposed to improve the capability of the electrode to serve both as a cathode and as an anode.

Figure 4:
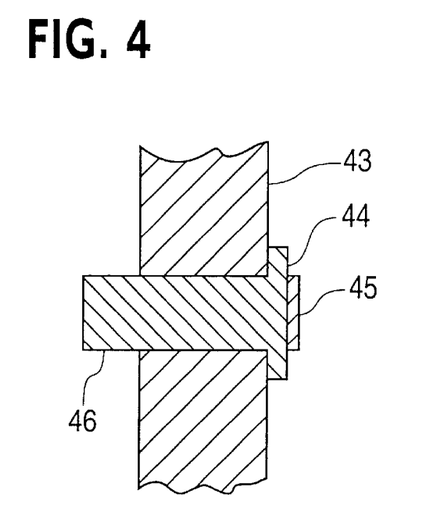
FIG. 4 is a schematic cross-sectional view of an electrode of a third embodiment of an x-ray tube according to the present invention.

An electrode according to this third embodiment is shown in FIG. 4 as a cut-out view of enlarged scale of an x-ray tube according to the invention. In FIG. 4 is shown a section of an x-ray tube end wall 43 through which an electrode 46 extends.

Figure 5:
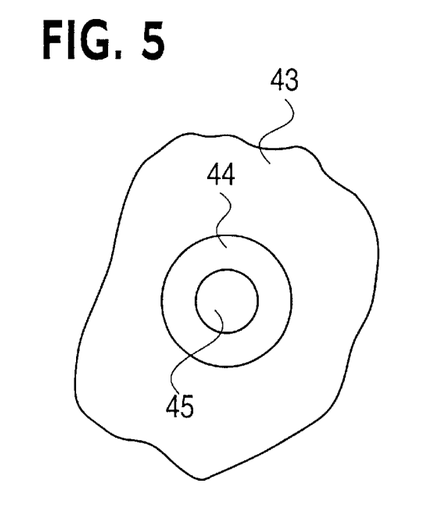
FIG. 5 is a side view of the electrode of FIG. 4.

At the vacuum side of the end wall, as is also shown in the side view of FIG. 5, the electrode is widened to a flange-shaped end portion 44. The electrode and, in consequence, the end portion 44 is made from a comparatively heavy material suitable as a target material, such as gold, platinum, tungsten, iridium or an alloy such as tungsten-thorium. Disposed on the end portion 44 is a thin layer 45 of a material suitable as an electron emitting material, such as diamond, tungsten, graphite or a ferro-electrical material. The emitting material could cover the entire end portion 44 or only a part of it, and could also be formed as a tip or similar (not shown). The emitting material layer is thin in order to allow electrons impacting onto the same to pass through with low energy loss.

It should of course be understood that instead of being formed with a flange, as is shown in FIG. 5, the electrode could have any other suitable form, such as cylindrical without any flange or having a generally polygonal cross section.

According to a fourth embodiment of the present invention, another design of electrodes serving as cathodes and anodes, alternatively, is provided in the x-ray tube. More specifically, according to the fourth embodiment electrode materials are selected and geometrically disposed on different distances in order to improve the electrode's capability to serve both as a cathode and as an anode.

Figure 6:
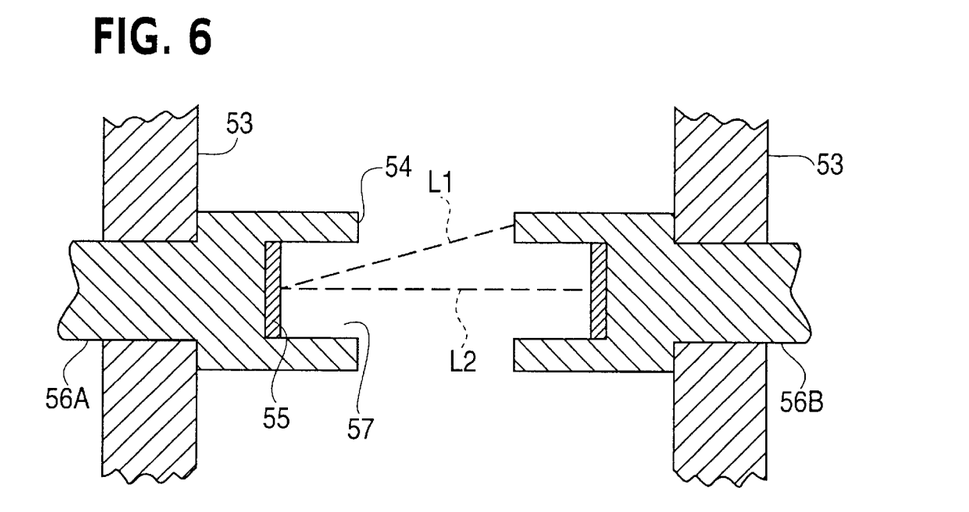
FIG. 6 is a schematic cross-sectional view of a pair of electrodes of a fourth embodiment of the present invention.

This is illustrated with the example of FIG. 6, wherein the electrodes 56A, 56B of an x-ray tube according to the invention are illustrated. Each electrode 56A, 56B has a generally cup-formed shape at the vacuum side of the enclosure 53 of the x-ray tube. The electrode 56B is generally identical to the electrode 56A. The target surface 54 of the electrode surrounds a central recess 57. The bottom of the recess 57 acts as the emitting surface of the electrode, and is preferably covered with a material 55 suitable for emitting electrons, as is described with the third embodiment above.

As is shown in FIG. 6, the distance Li from the electron emitting recess bottom of one electrode to the annular short end of the other electrode could be made considerably shorter than the distance L2 from the electron emitting recess bottom of one electrode to the electron emitting recess bottom of the other electrode. Consequently, when an electrical potential is applied across the electrodes, electrons emitted from the material 55 at the bottom of a recess tend to hit the other electrode at its annular short end 54, since the difference in distances results in higher electric field strength near the annular end 54 of the receiving electrode than near the recess bottom of that electrode.

Therefore, by forming the end surface 54 from a material suitable as a target material x-ray radiation will be produced at that surface. Preferably, when selecting the material, of the end surface 54 its ability not to emit electrons should also be considered. At the same time, the electron emitting material 55 at the bottom of the recess 57 will be saved from excessive electron bombardment, thereby prolonging the lifetime of this part of the electrode.

Figure 7:
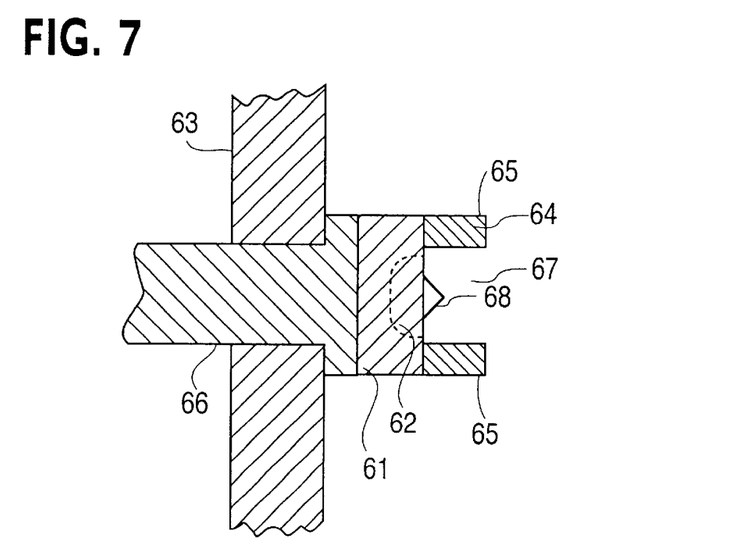
FIG. 7 is a schematic cross-sectional view of an electrode of a fifth embodiment of the present invention.

In a fifth embodiment of the present invention, as is illustrated in FIG. 7, a similar effect of improved electrode lifetime is achieved by designing the electrodes to control the path of the electrons towards target materials.

With reference to FIG. 7, each electrode has, at the vacuum side end of a connector portion 66 (formed by a suitable conducting material, such as copper), a semiconductor section 61 connected thereto. A generally annular body 65 of a target material, having a central opening 67, is connected to the semiconductor section 61. The target body 65 exhibits a target surface 64 toward the other electrode (not shown in FIG. 7).

In the central opening 67, and connected to the semiconductor section 61, is disposed a structure for emitting electrons, shown in FIG. 7 as a pyramid-shaped diamond 68 although other structures such as a thin diamond or tungsten plate are possible as well.

The semiconductor section 61 is made from n-doped silicon. However, a portion 62 generally forming the bottom of the recess formed by the opening 67 is formed from p-doped silicon. These portions are so arranged that the p-doped silicon portion 62 has no direct electrical contact with the target 64, and the n-doped silicon has direct electrical contact with the target 64 but not with the electron emitting structure 68.

Thus, with the arrangement according to the fifth embodiment the electron emitting portion 68 of the electrode is positioned on a semiconductor pn-junction, forming a diode.

It should be noted that it is not necessary to arrange the electrode such that it exhibits a recess accommodating the semiconductor material, like the recess formed by the central opening 67 of the embodiment shown in FIG. 7. It is possible to dispose the semiconducting material substantially in level with a target surface.

Figure 8:
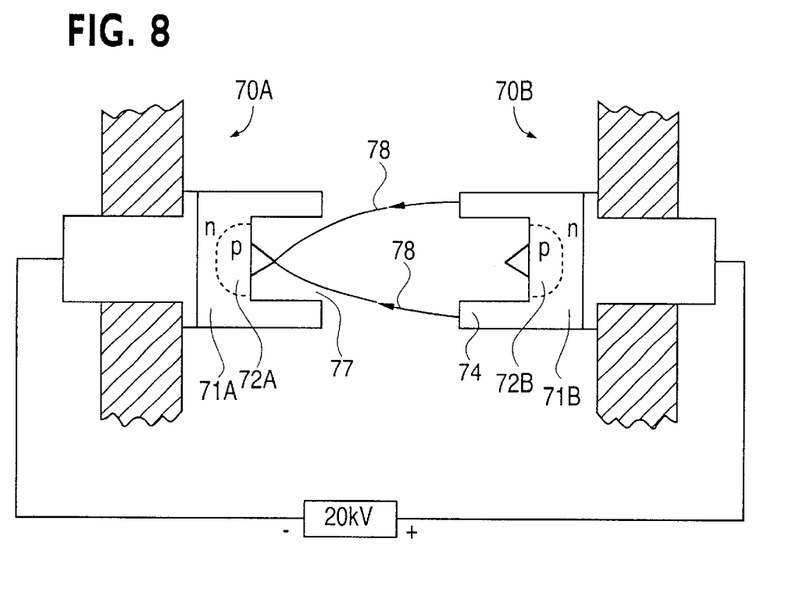
FIG. 8 is a schematic cross-sectional view of an x-ray tube in a state of operation (and wherein some sectional lines have been omitted for clarity).

In FIG. 8 is illustrated the use of electrodes according to the invention to guide the electrical field, and consequently the electron beams.

This makes it possible to force incoming electrons away from the electron emitting material and toward the target material, as will now be described with reference to FIG. 8.

In FIG. 8 is shown an electrode 70A in a state where it acts as a cathode, and an electrode 70B in a state where it acts as an anode, both electrodes being of the embodiment described with reference to FIG. 7. It should of course be understood that during a subsequent interval the electrode 70A will act as anode while the electrode 70B will act as cathode, according to the present invention.

A high voltage, such as 20,000 V, is applied across the electrodes, whereby the electrode 70A is negative with respect to the other electrode 70B. Thus, electrode 70A acts as cathode and electrode 70B as an anode, respectively.

At the cathode, i.e. electrode 70A, the pn-junction will experience a minor voltage drop (typically less than 1 V) between the p-doped portion 72A and the n-doped portion 71A, the n-doped region 71A having the lower potential. Thus, the pn-junction will become forward biased and in this state it acts as a conductor.

At the same time, the pn-junction of the other electrode 70B, acting as an anode, will be reverse biased. In this state, a depletion region will be formed between the p-doped portion 72B of the electrode 70B and the n-doped portion 71B. The diode formed by the p-doped and the n-doped portions, respectively, will therefore act as an isolator.

In consequence, an electric field is established between the electrodes 70A and 70B, as suggested by the dotted lines 78. This field distribution will urge a majority of the electrons emitted from electrode 70A to be guided by the electric field to hit the target surface 74. When the electron hits the target surface 74, x-ray energy is emitted.

When the polarities are switched the electrodes 70A, 70B will work correspondingly in the other direction.

Figure 9:
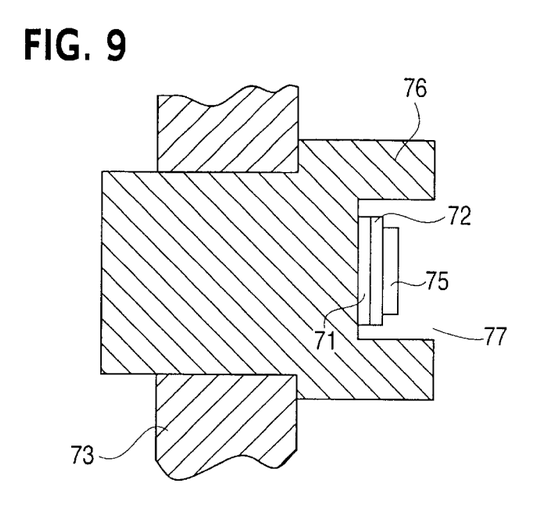
FIG. 9 is a schematic cross-sectional view of an electrode of a sixth embodiment of an x-ray tube according to the present invention.

A sixth embodiment of the present invention is shown in FIG. 9. The working principle is the same as for the fifth embodiment, but a simplified design is provided. As for the fourth and fifth embodiments, the vacuum side end of the electrode according to FIG. 9 is formed to a cup-like shape having a generally cylindrical recess 77 at its end. The electrode body is made from a suitable metal, such as gold, platinum or tungsten.

At the bottom of the recess 77 is attached a pn-diode (formed of an n-doped silicon layer 71 next to the recess bottom and a p-doped silicon layer 72, respectively), and an electron emitting material 75 covers the pn-diode.

While operating according to the same principle as the fifth embodiment, the electrode of the sixth embodiment is assessed to provide a simpler manufacturing process, and thus a lower cost.

It should be noted that the science and technology for forming high voltage diodes, achieving good electrical semiconductor junctions, good electrical contacts between semiconductor and metals, as well as other necessary manufacturing processes are considered to be well known for anyone skilled in the art.

Figure 12:
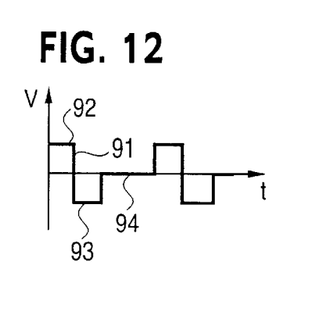
FIG. 12 is a voltage vs. time diagram showing an example of a supply voltage.

The power supply for feeding an alternating high voltage to the x-ray tube according to the invention could be any suitable conventional power supply. Although many wave forms are possible, a useful voltage supply is an essentially square-shaped voltage alternating between a positive and a negative voltage. In FIG. 12 is shown a voltage vs. time diagram showing a presently preferred supply voltage 91, having a high positive voltage level 92 such as +20,000 V, followed by a corresponding negative voltage level 93 such as −20,000 V which is followed by a dwell time at approximately 0 V. By selecting a suitable dwell time between the cycles of alternating voltage, the temperature of the electrodes could be controlled with respect to the level of the voltage applied during the high and low levels.

As is generally known, even when two electrodes are manufactured to be identical to very close tolerances, there will still remain very small differences that will result in somewhat different characteristics. In addition, normal operation induces such differences due to the sensitivity of the emission process to local electrical field strength. Such differences could change in time, due to the erosion occurring at the electrodes. In consequence, at a given potential of the same magnitude the two electrodes will not emit exactly the same current. A difference in current will result in different dose rates delivered, depending on which electrode is acting as emitter.

It is desirable to keep the applied potential at a fairly constant magnitude in order to keep the energy spectrum of the emitted radiation fairly constant. Therefore, it could be desirable not to excessively change the potential to correct for the differences in current. At the same time, it is important to keep the dose rate essentially the same regardless of which one of the electrodes that is emitting the x-ray radiation.

Instead, the power source for use with an x-ray tube of the present invention can be provided with means for controlling the dose rate provided by each electrode in such a way that substantially the same x-ray dose rate is emitted from each electrode. Such means include a unit for monitoring the current consumption, a calculating unit for integrating the current consumption over time and a unit for controlling the timing of the switching of the electrode potential.

Figure 14:
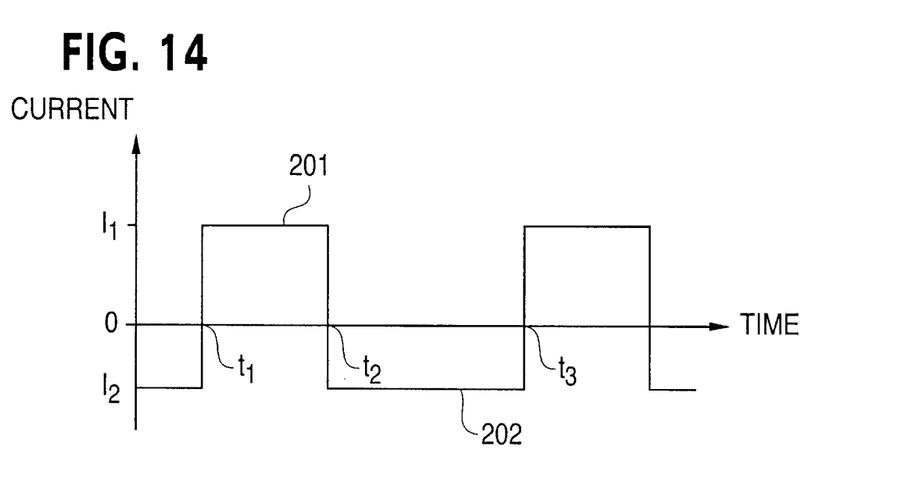
FIG. 14 is a current vs. time diagram for an embodiment of an x-ray system of the present invention, wherein the electrode potential switching is controlled by measuring the power consumption at each electrode.

In FIG. 14 this is illustrated (in an exaggerated manner) with a chart showing the current intensity as a function of time. The chart is idealised in that the current intensity, which is shown as being generally constant between each switching point, in the reality will fluctuate visibly.

During a switching cycle, at a first point in time t1 one electrode of the electrode pair is powered as the anode, and the current output i(t) 201 reaches an intensity of I1. At a second point of time t2 the power source is switched, and the other electrode of the electrode pair is powered as the anode. Between the time t2 and the time t3, where the power source again switches to return the first electrode to the anode state, the current output i(t) 202 reaches an intensity of I2, being of reversed potential with respect to I1.

The power source continuously controls the switching instances t1, t2, t3 in such a way that the delivered current, being proportional to the delivered dose rate, between each switching instance is substantially the same for each electrode. This could be expressed with the formula $$\int_{t_1}^{t_2} \text{ABS}(i)dt = \int_{t_2}^{t_3} \text{ABS}(i)dt$$

Similarly, in order to even better control the x-ray output, the switching operation could be based on a measurement of the x-ray radiation emitted at each electrode. In this way, it is also possible to account for geometrical differences on, or close to, each pair of radiating elements, as well as differences in tube wall thickness or composition, mounting tolerances, differences in electrode geometry etc.

Figure 15:
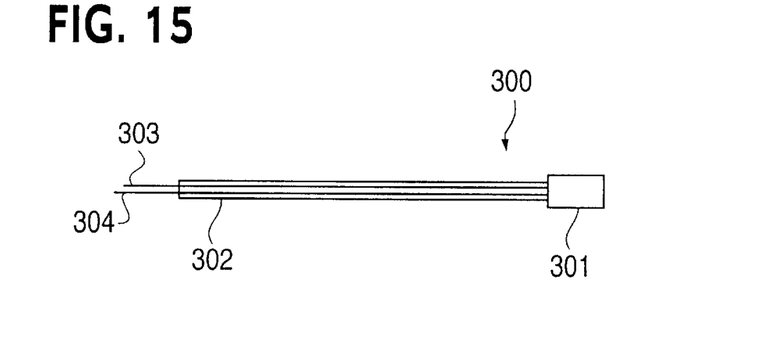
FIG. 15 is a schematic view of a device for inserting an x-ray tube according to the present invention into a body.

In FIG. 15 is shown a device 300 for insertion into a human body, wherein a miniaturized x-ray tube 301 according to the invention is attached at, or near, the distal end of an elongated guiding member 302, such as a cable with suitable mechanical properties (stiffness etc.) or a needle. Thus, the guiding member serves to insert the x-ray tube into the body. Also, the electrical leads 303, 304 are provided through the guiding member, such as the cable or the needle. Care has to be taken to insulate the high voltage portions from the patient. The applicant has found that small diameter wires (approximately 1 mm) with FEP insulation in several layers easily will be able to withstand these high voltages.

As is known within the art of inserting devices into vessels inside the body, a guiding lumen (not shown) is preferably used in order to position the device. The lumen is used to thread the device onto an already placed guide wire, and the device is steered into the correct position by this method.

In addition to the advantages described above, a miniature x-ray tube according to the present invention could be manufactured easily and inexpensively due to very few components. One reason for this is the possibility to use identical electrodes at both sides of the x-ray cell.

Of course, several modifications of an x-ray tube according to the inventions are possible. For example the x-ray tube could include grids, well known in themselves, to form a triode.

What is claimed is:

1. A device for providing x-ray irradiation to a site for treatment inside a human body, comprising:
   an elongated guiding member having a distal and a proximal end, and electrical leads, wherein
   a miniaturized x-ray tube is mounted at the distal end of the elongated guiding member wherein said x-ray tube includes a first electrode and a second electrode, each one of the first and the second electrodes respectively being connectable to a high voltage source via the leads to alternatingly act as an anode and as a cathode.

2. The x-ray tube according to claim 1, wherein the first and the second electrodes each comprises a body made from a target material for emitting x-ray radiation when hit by electrons, and wherein each electrode is provided with an emitting material for emitting electrons in response to an electrical potential applied to the electrode.

3. The x-ray tube according to claim 2, wherein said target material is selected from the group consisting of gold, tungsten, platinum, iridium and a tungsten-thorium alloy.

4. The x-ray tube according to claim 2 or 3, wherein said emitting material is selected from the group consisting of diamond, tungsten, graphite and ferro-electrical material.

5. The x-ray tube according to claim 1, wherein at least one of the electrodes is provided with a recess at an electron and x-ray emitting end, said recess at its bottom being provided with an emitting material for emitting electrons in response to an electrical potential applied to the electrode.

6. The x-ray tube according to claim 1, wherein at least one of the electrodes comprises a pn-diode, said pn-diode being forward biased when th e electrode acts as a cathode and reverse biased when the electrode acts as an anode.

7. The x-ray tube according to claim 1 further comprising at least a second set of electrodes, the electrodes of the second set being configured to act as anodes and cathodes, alternately.

8. The device according to claim 1, wherein the elongated guiding member is a needle.

9. The device according to claim 1, wherein the elongated guiding member is a cable.

10. A system for radiation treatment of a site inside a living body, comprising:

an elongated guiding member having a distal and a proximal end and electrical leads, wherein in a miniaturized x-ray tube is mounted at the distal end of the elongated guiding member;

said x-ray tube having at least two electrodes; and a power source connected to the electrodes via the leads, wherein the power source comprises a switching unit for providing a voltage of switching polarities across the electrodes, each electrode thereby acting as anode and cathode, alternately.

11. The system for radiation treatment according to claim 10, wherein said power source comprises:

a monitor to monitor current consumption at each electrode, an integrator to integrate the current consumption over time, and a controller to control timing of the switching unit based on integrated current consumption.

12. A method for treatment of diseases inside a living body, comprising the steps of:

connecting a power source to a miniature x-ray tube for providing an electric potential across electrodes of the x-ray tube for creating x-ray radiation, and introducing the miniature x-ray tube into an area for treatment inside the living body, wherein the electrical potential is switched to alternatingly operate the electrodes as anodes and cathodes.

13. The method according to claim 12, further including the step of providing a dwell time between cycles of alternating voltages.

14. The method according to claim 12, further comprising the steps of:

measuring integrated current consumption between consecutive electrical potential switching operations, and initiating switching of electrical operation based on the measured integrated current consumption.

15. The method according to claim 14, wherein switching operation is controlled such that current consumption at each electrode, respectively, is substantially the same within a switching cycle.

* * * * *